US009523661B2

(12) United States Patent
Yoon et al.

(10) Patent No.: US 9,523,661 B2
(45) Date of Patent: Dec. 20, 2016

(54) METHOD AND APPARATUS FOR LOCATING A SOURCE OF DAMAGE IN A LARGE COMPOSITE MATERIAL STRUCTURE

(75) Inventors: Dong Jin Yoon, Daejeon (KR); Byeong Hee Han, Namwon-si (KR); Young Joo Kim, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 885 days.

(21) Appl. No.: 13/817,153

(22) PCT Filed: Aug. 17, 2011

(86) PCT No.: PCT/KR2011/006045
§ 371 (c)(1),
(2), (4) Date: Mar. 25, 2013

(87) PCT Pub. No.: WO2012/023802
PCT Pub. Date: Feb. 23, 2012

(65) Prior Publication Data
US 2013/0191040 A1    Jul. 25, 2013

(30) Foreign Application Priority Data
Aug. 17, 2010  (KR) .................. 10-2010-0079075

(51) Int. Cl.
*G01N 29/44*    (2006.01)
*G01N 29/06*    (2006.01)
(Continued)

(52) U.S. Cl.
CPC ............ *G01N 29/44* (2013.01); *G01N 29/069* (2013.01); *G01N 29/14* (2013.01); *G01N 29/42* (2013.01);
(Continued)

(58) Field of Classification Search
CPC ..... G06T 1/005; G06T 11/203; G05D 1/0221; H02G 1/1253; G01M 11/086; G01M 5/0033; G01H 1/14; A61B 5/002
(Continued)

(56) References Cited

U.S. PATENT DOCUMENTS 4,193,075 A * 3/1980 Blazek .................. G01S 1/54
342/398
5,214,960 A * 6/1993 Tsuboi .................. G01H 1/14
702/39
(Continued)

FOREIGN PATENT DOCUMENTS

CN          101042372        9/2007
JP         2003232782   *   8/2003   ........... G01N 29/14
(Continued)

OTHER PUBLICATIONS

International Search Report—PCT/KR2011/006045 dated Mar. 9, 2012.

*Primary Examiner* — Andrew Schechter
*Assistant Examiner* — Kaleria Knox
(74) *Attorney, Agent, or Firm* — STIP Law Group, LLC

(57) ABSTRACT

Provided is a method of locating a damage source of a wind turbine blade for tracking a damage source location of a blade used in a wind power generator, and more particularly, a method of locating a damage source of a wind turbine blade and an apparatus thereof in a large composite material structure capable of accurately locating a damage source even in a large composite material structure by detecting defects using contour maps written based on elastic wave energy value. The method of locating a damage source of the wind turbine blade according to the present invention can accurately locate the damage source even in the large composite material structure using at least two materials unlike the related art and can use a smaller number of AE sensor than the related art.

6 Claims, 9 Drawing Sheets

(51) Int. Cl.
*G01N 29/14* (2006.01)
*G01N 29/42* (2006.01)

(52) U.S. Cl.
CPC ............... *G01N 2291/0231* (2013.01); *G01N 2291/2693* (2013.01)

(58) Field of Classification Search
USPC ...... 345/441; 180/169; 73/587, 582; 33/290; 83/522.12; 342/398; 702/39, 36; 250/227.14; 340/870.3
See application file for complete search history.

(56) References Cited

U.S. PATENT DOCUMENTS

| | | | | |
|---|---|---|---|---|
| 5,287,441 | A * | 2/1994 | Nakamura | G06T 11/203 345/441 |
| 6,205,380 | B1 * | 3/2001 | Bauer | G05D 1/0221 180/169 |
| 6,477,276 | B1 * | 11/2002 | Inoue | G06T 1/005 375/E7.075 |
| 8,024,866 | B2 * | 9/2011 | Chiorean | G01C 15/06 33/290 |
| 2005/0067559 | A1 * | 3/2005 | Ogisu | G01M 11/086 250/227.14 |
| 2006/0032313 | A1 * | 2/2006 | Austin | G01H 1/00 73/587 |
| 2009/0201172 | A1 * | 8/2009 | Edell | A61B 5/0002 340/870.3 |
| 2010/0077899 | A1 * | 4/2010 | Yano | H02G 1/1253 83/522.12 |
| 2011/0314915 | A1 * | 12/2011 | Adams | G01M 5/0033 73/582 |

FOREIGN PATENT DOCUMENTS

| | | |
|---|---|---|
| JP | 2004170397 | 6/2004 |
| KR | 100894430 | 4/2009 |
| KR | 1020100053867 | 5/2010 |

* cited by examiner (a)

(b)

(c)

METHOD AND APPARATUS FOR LOCATING A SOURCE OF DAMAGE IN A LARGE COMPOSITE MATERIAL STRUCTURE

TECHNICAL FIELD

The present invention relates to a method of locating a damage source of a wind turbine blade for tracking a damage source location of a blade used in a wind power generator, and more particularly, to a method of locating a damage source and an apparatus thereof in a large composite material structure capable of accurately locating a damage source even in a large composite material structure by detecting defects using contour maps written based on elastic wave energy.

BACKGROUND ART

Since wind power energy is a power generation field having the largest occupancy rate as new renewable energy along with solar energy and is being expanded in a large capacity and offshore wind power field, a blade 3 is getting larger, such that a need for monitoring the health of the blade 3 has been increased.

FIG. 1 illustrates a general wind power generator 1. The wind power generator 1 is an apparatus that is mounted in a mountainous or at sea where wind velocity is kept to some extent to produce electricity using wind and has a rotatably controlled nacelle 4 disposed at an end of a tower 2 and a plurality of wind turbine blades 3 disposed at a rotation shaft 6 of the nacelle 4. An inside of the nacelle 4 is a generator (not illustrated) interposed in the rotation shaft 6 via a reducer (not illustrated) and is configured to allow a power generator to produce electricity while the blade 3 rotates by wind power.

In order for the wind turbine blade 3 to have high power generation capacity, the large wind turbine blade 3 is essentially required. For example, in case of the wind power generator of 750 kW, one of the lengths of the blades 3 becomes 25 m and in case of the wind power generator of 3 MW, a length of the blade 3 is suddenly increased to 45 m. As the blade 3 is large, a ratio of rigidity to high weight effectively is required. In order to effectively reduce the increase in weight and secure the rigidity ratio for coping with the increase in the size of the blade, industries have positively used a composite material.

As the composite material, glass fiber reinforced plastic (GFRP) and PVC/Balsawood are frequently used. In order to support a wind load and a self-weight, a method of reducing a weight by allowing a central portion of the blade 3 at which a shear web is located to use the GFRP having high rigidity and the remaining portion at which an aerodynamic structure to have a GFRP skin filled with the PVC or the Balsawood has been used. Further, a difference between a material thickness around a root of the blade 3 that is in particular subjected to a big load and a material thickness around a tip 5 of the blade 3 that is not subjected to a load is large.

The increase in the size of the wind turbine blade 3 essentially requires a development of a nondestructive all time defect monitoring technology. The problem of the size of the wind turbine blade 3 and the installation location of the wind power generator 1 is fundamentally impossible to perform maintenance in a laboratory in terms of disassembly. The above problem is importantly considered in that the destruction of the blade 3 due to the damage may lead to a big accident and damage other wind power generators 1 that are installed around the wind power generator 1.

The damage of the wind turbine blade 3 may occur due to several causes. The manufacturing of the wind turbine blade 3 representatively uses an infusion method of laminating a composite material, putting the laminated composite material in a mold, and permeating an adhesive resin thereinto. The damage may occur in the incomplete permeation of the adhesive resin during an infusion process and the separation of an adhesive occurring during an adhesive process of each component completed during the infusion process. Further, the damage may occur due to the external impact during a process of transporting a giant structure to an actual installation place. In addition to the defects, the damage may occur due to a peeling of the composite material according to a sudden change in a wind load during the actual driving, a crack due to a collision of an external object, and a natural disaster such as lightning, hail, typhoon, and the like.

A technology of locating acoustic emission devised to measure a tendency of damage occurrence of a pressure container, a bridge, and a concrete structure measures elastic waves propagated through a material using a plurality of sensors and searches for a damage source location using a location of a sensor and a time difference of arrival of the elastic waves. Therefore, attempts for applying a nondestructive inspection technology to the wind turbine blade 3 have been conducted recently.

FIG. 2 illustrates a method of locating a damage source using acoustic emission according to the related art. The method according to the related art roughly searches for occurrence locations of cracks by surrounding a portion to be damaged in the structure to be monitored, installing a plurality of acoustic emission (AE) sensors s1, s2, s3, and s4, detecting an acoustic emission (AE) signal, amplifying the AE signal by a signal analysis equipment C, and analyzing the AE signal.

However, the foregoing related art uses the time difference until the elastic wave reaches the AE sensors s1, s2, s3, and s4, and therefore shows satisfactory results for isotropic materials of the same material, but causes a lot of difference for a large wind turbine blade 3, and the like, due to a change in a material and a difference in a propagation speed of an elastic wave according to an elastic wave direction. That is, the related art has a problem in that it is difficult to track the damage source location in the structure formed of at least two composite materials due to greatly varying physical property values of material determining the elastic wave propagation speed.

DISCLOSURE

Technical Problem

An object of the present invention is to provide a method of locating a damage source and an apparatus thereof using acoustic emission capable of easily searching for a damage source location of a large composite material structure (for example, a wind turbine blade 30) formed of a composite material with high accuracy.

Technical Solution

In one general aspect, there is provided a method of building a contour map for a damage source location in a nondestructive way using acoustic emission, including: a first step of attaching at least two AE sensors 200 within a portion to be located; a second step of generating a test location 910 in a structure to be located; a third step of applying elastic waves to each test location 910; a fourth step of measuring AE signal by each AE sensor 200; a fifth step of transforming the measured AE signal into time or frequency and then into a energy value; and a sixth step of databasing the transformed energy value as a parameter of information on the test position 910.

The second step may include a 2-1 step of partitioning the test location into a lattice type using the AE sensor 200 and a 2-2 step of selecting cross points of each lattice as the test location 910.

After the sixth step, the method of building a contour map for a damage source location includes a seventh step of extending the number of databased energy value data and databasing the extended energy value data again.

In the seventh step, data extension may be made by dividing the test locations 910 at a plurality of intervals and interpolation may be performed based on an energy value at the test location 910.

In the third step, a size of elastic waves applied to the test locations 910 may be changed and applied and in the sixth step, the test locations 910 may be a database according to the size of the elastic waves.

In another general aspect, there is provided a method of locating a damage source in a nondestructive way using acoustic emission, including: a first step of applying an elastic wave to test locations 910 of a structure to be located to database measured energy values as the test locations 910 for each AE sensor 200; a second step of attaching the plurality of AE sensors 200 to a structure applied to an actual environment to monitor acoustic emission; a third step of transforming a signal into an energy value when the AE signal is input; a fourth step of calling the data base of the first step to extract test locations corresponding to the energy values as the damage location prediction regions for each AE sensor 200; and a fifth step of overlaying damage source prediction regions to obtain cross points and determining the cross points as damage occurrence locations.

When the cross points are not obtained in the fifth step, an error range may be given to the elastic energy values of the third step to transform the given elastic energy value into a new elastic energy value and may include the sixth step of the damage prediction region extension returning to the fourth step again.

The elastic waves of the first step may be applied in different sizes so as to be databased and the damage prediction region extension of the sixth step may be formed for each database for the size of the elastic waves, such that the final damage occurrence locations are determined from the database having a minimum error range.

In still another general aspect, there is provided an apparatus of locating a damage source in a nondestructive way using acoustic emission, including: an AE sensor 200 that detects an acoustic emission signal; an amplification unit 300 that amplifies the detected AE signal to an analyzable size; a signal processor 400 that processes the amplified AE signal; an origination module 500 that originates the signal processed AE signal in a wired line or wireless; a receiving module 700 that receives the AE signal from the origination module 500 and transmits the received AE signal to a signal analysis unit 800; and a signal analysis unit 800 that receives the AE signal from the receiving module 700 to locate a damage source.

The originating module 500 may include an originating antenna 510 that originates the AE signal in wireless.

The receiving module 700 may include a receiving antenna 710 that receives the AE signal in wireless.

In still yet another general aspect, there is provided a method of locating a damage source in a nondestructive way using acoustic emission, including: a first step of attaching at least two AE sensors 200 within a portion to be located; a second step of generating test locations 910 in a structure to be located; a third step of applying elastic waves to each test location 910; a fourth step of measuring AE signals with each AE sensor 200; a fifth step of transforming the measured AE signals into time or frequency and then transforming the transformed AE signals into energy values; a sixth step of databasing the transformed energy values as parameters of information on the test locations 910; a seventh step of attaching the plurality of AE sensors 200 to a structure applied to the actual environment to monitor acoustic emission; when the AE signals are input, an eighth step of transforming the signals into the energy values; a ninth step of calling a database of the sixth step to extract the called database as damage source prediction regions for each AE sensor 200 corresponding to the elastic energy of the eighth step; and a tenth step of overlaying the damage source prediction region to obtain cross points and determine the cross points as the damage source occurrence locations.

Advantageous Effects

According to the present invention, the method of locating a damage source in the large composite material structure can accurately locate the damage source even in the heterogeneous large composite material structure, unlike the related art.

Further, the method of locating a damage source in the large composite material structure can very facilitate the extension of the measured region, unlike the related art.

In addition, the method of locating a damage source in the large composite material structure can accurately locate the location of the wide region by the minimum AE sensor.

DESCRIPTION OF DRAWINGS

The above and other objects, features and advantages of the present invention will become apparent from the following description of preferred embodiments given in conjunction with the accompanying drawings, in which.

<Detailed Description of Main Elements>

| | |
|---|---|
| 100: Location Apparatus | 200: AE Sensor |
| 300: Amplification Unit | |
| 310: Pre-processing Amplifier | |
| 320: Main Amplifier | |
| 400: Signal Processor | |
| 500: Originating Module | 510: Originating Antenna |
| 600: Power Supply | 700: Receiving Module |
| 710: Receiving Antenna | |
| 800: Signal Analysis Unit | |
| 900: Sample | 910: Test Location |
| 920, 930, 940, 950: Damage Occurrence Prediction Region | |

[Best Mode]

Figure 3:
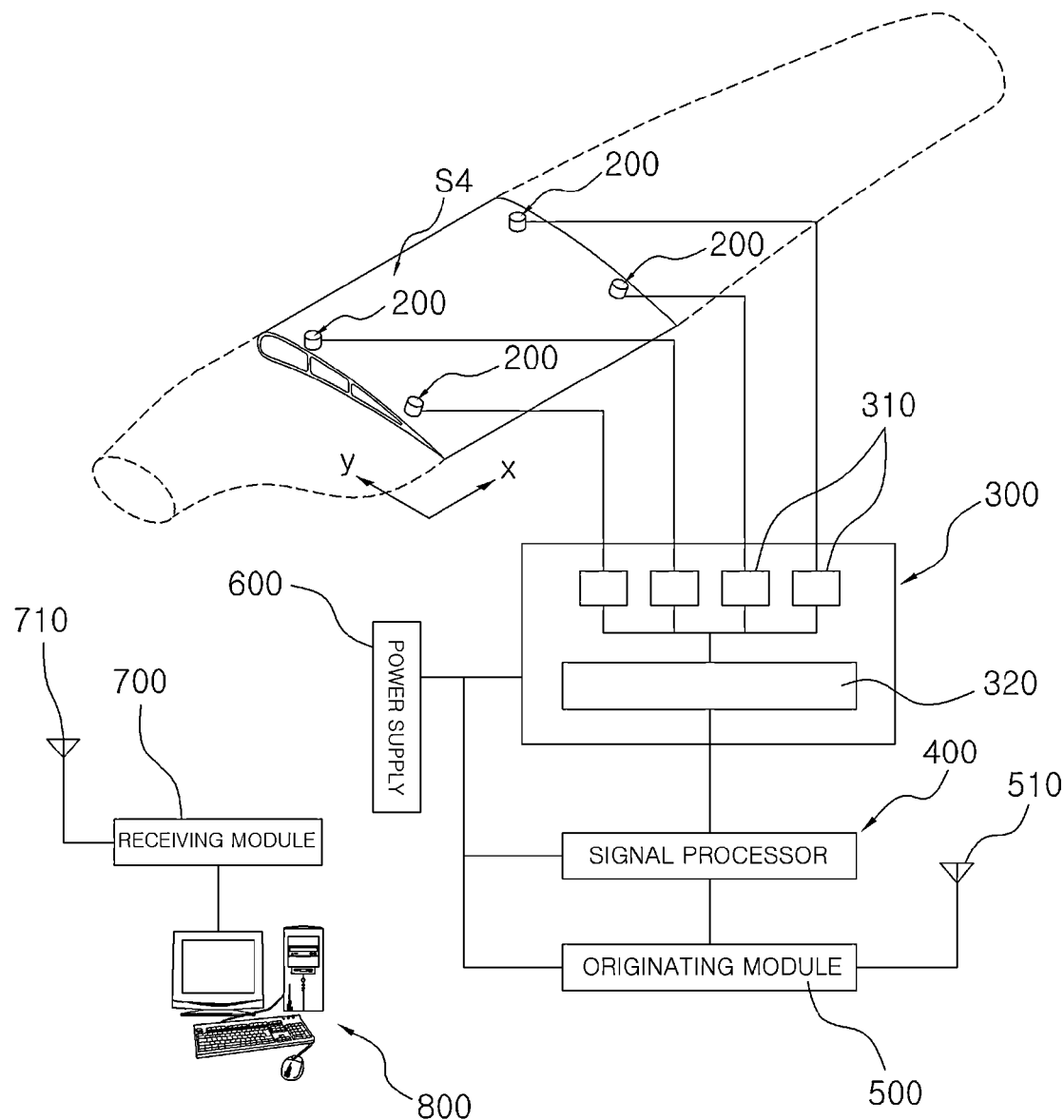
FIG. 3 is a schematic diagram illustrating an apparatus of locating a damage source of a wind turbine blade according to the related art.
Figure 4:
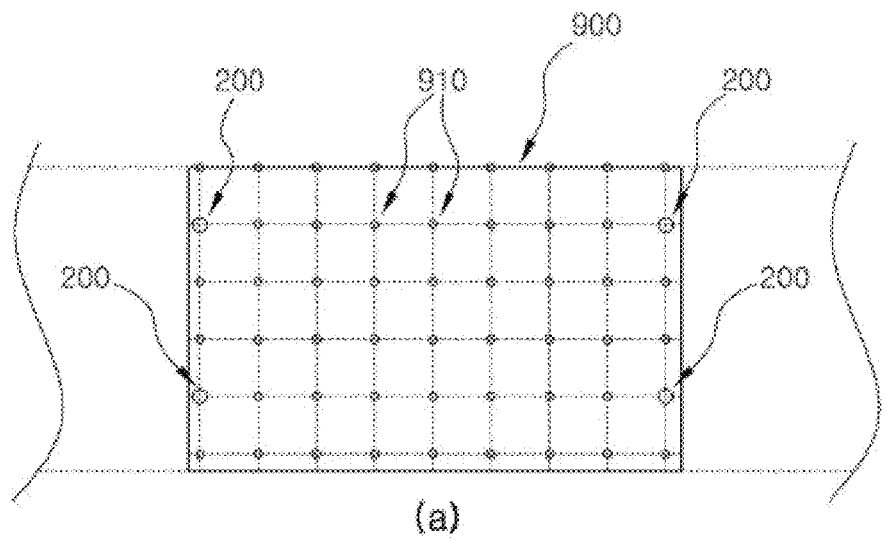
FIG. 4 is an exemplified diagram of a sample structure and contour maps for configuring a contour map database based on an energy value according to the present invention.
Figure 4:
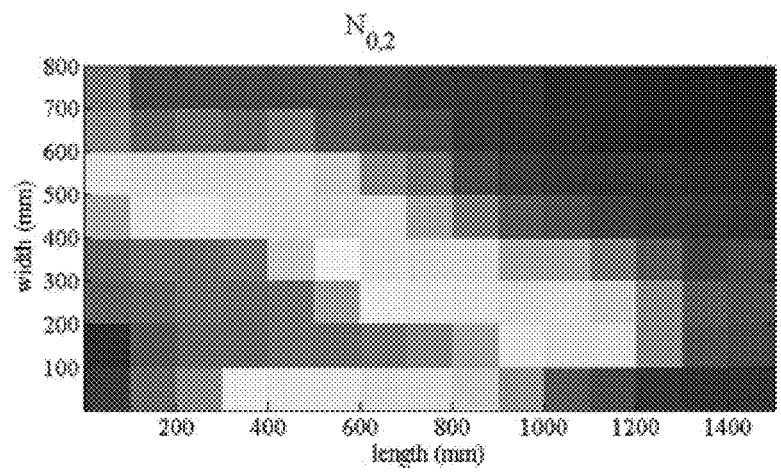
Figure 4:
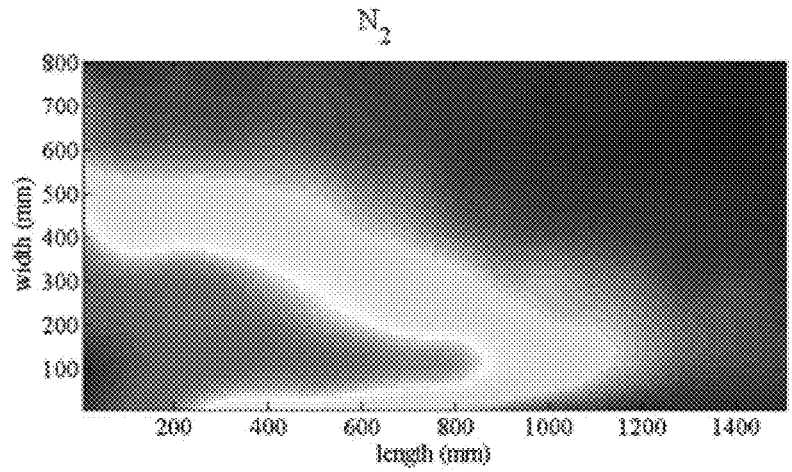
Figure 5:
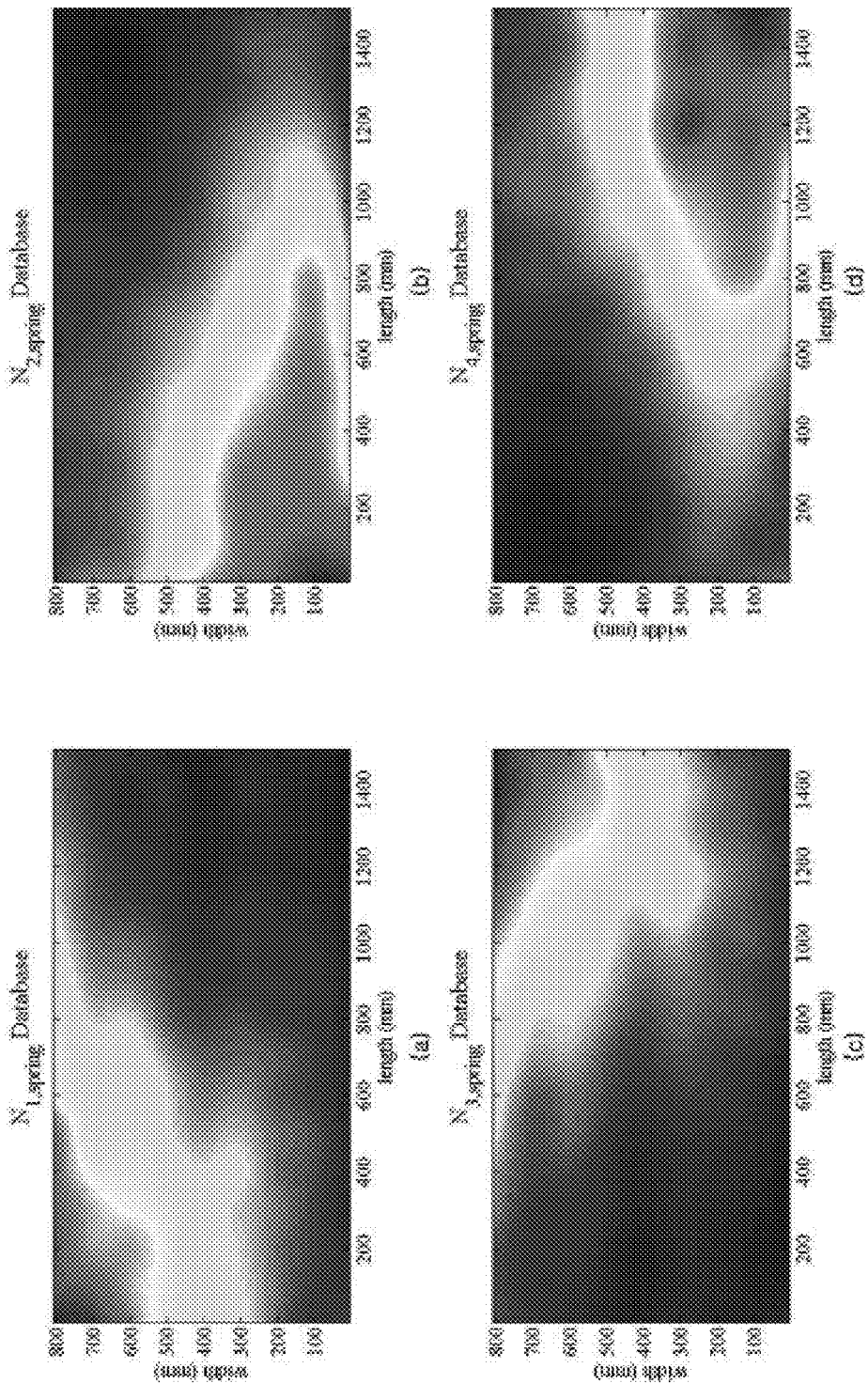
FIG. 5 is an exemplified diagram illustrating contour maps at each AE sensor of the method of locating a damage source according to the present invention.
Figure 6:
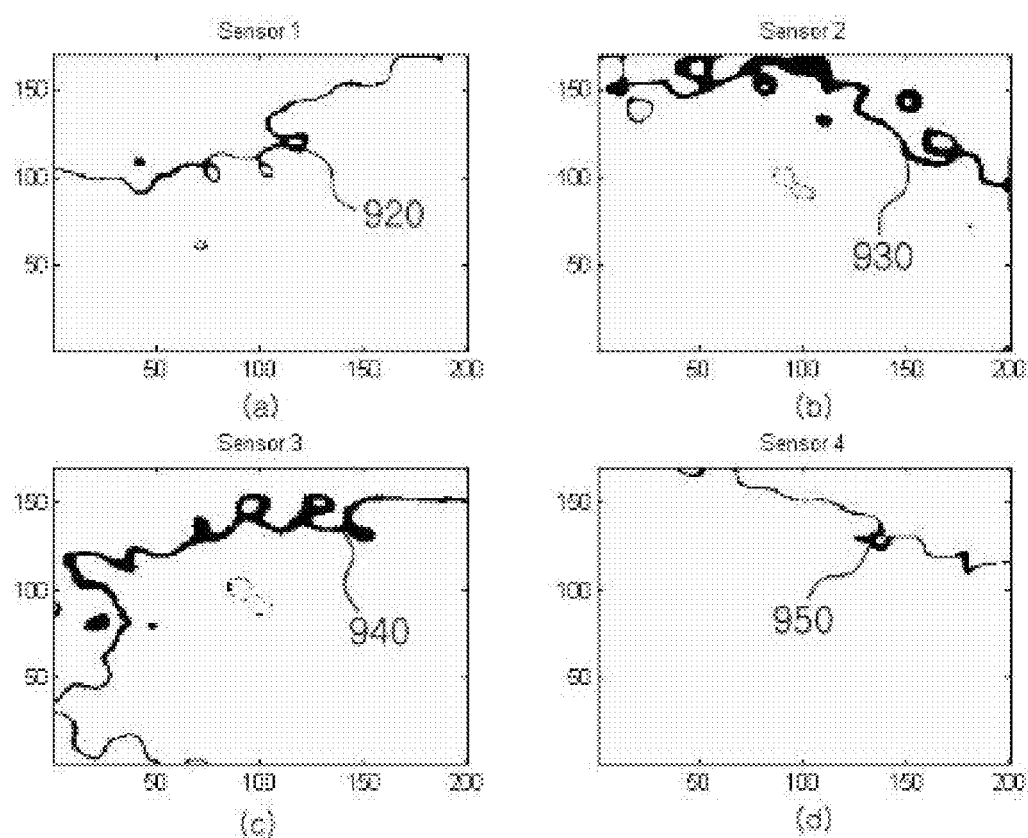
FIG. 6 is an exemplified diagram for describing a mechanism of determining a damage source location of the method of locating a damage source of a wind turbine blade according to the present invention.
Figure 7:
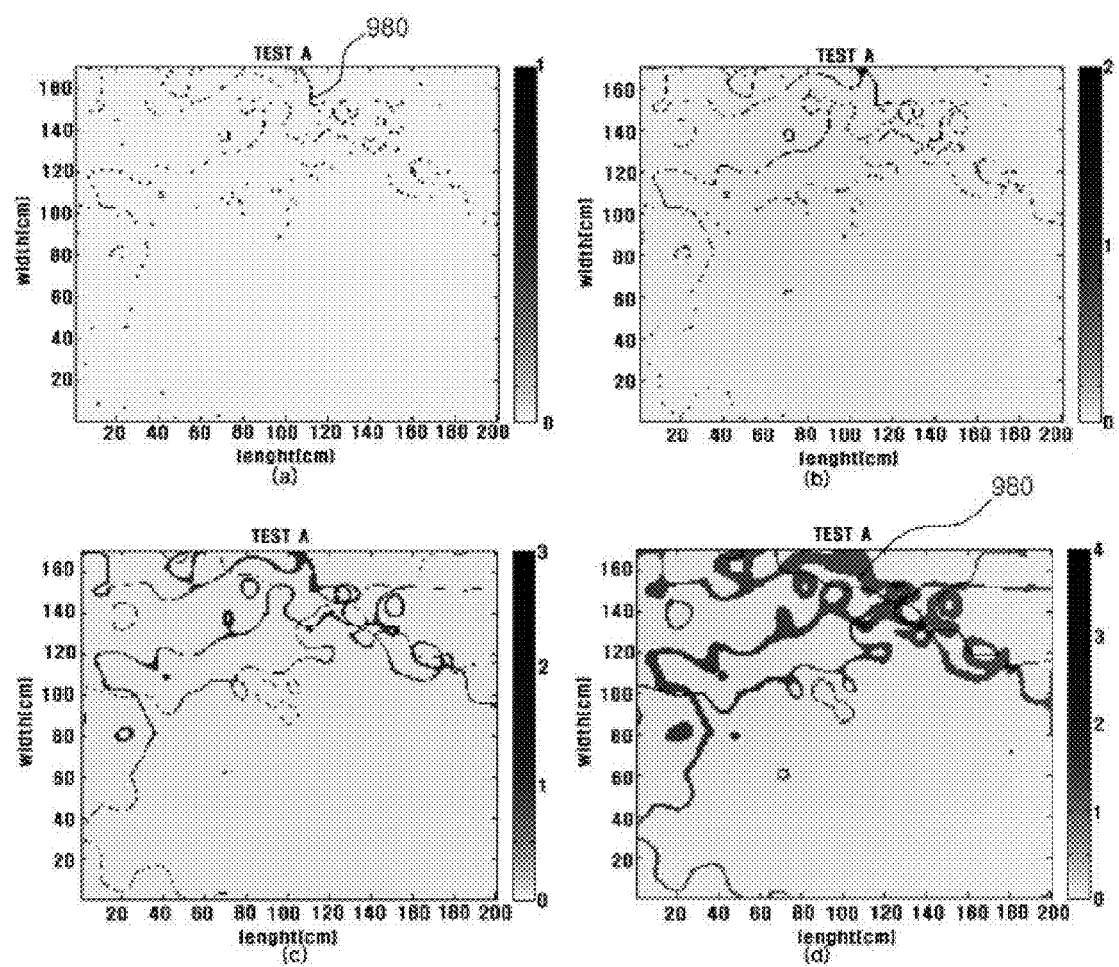
FIG. 7 is an exemplified diagram for describing a mechanism of expanding a damage source prediction region of the method of locating a damage source of the wind turbine blade according to the present invention.
Figure 8:
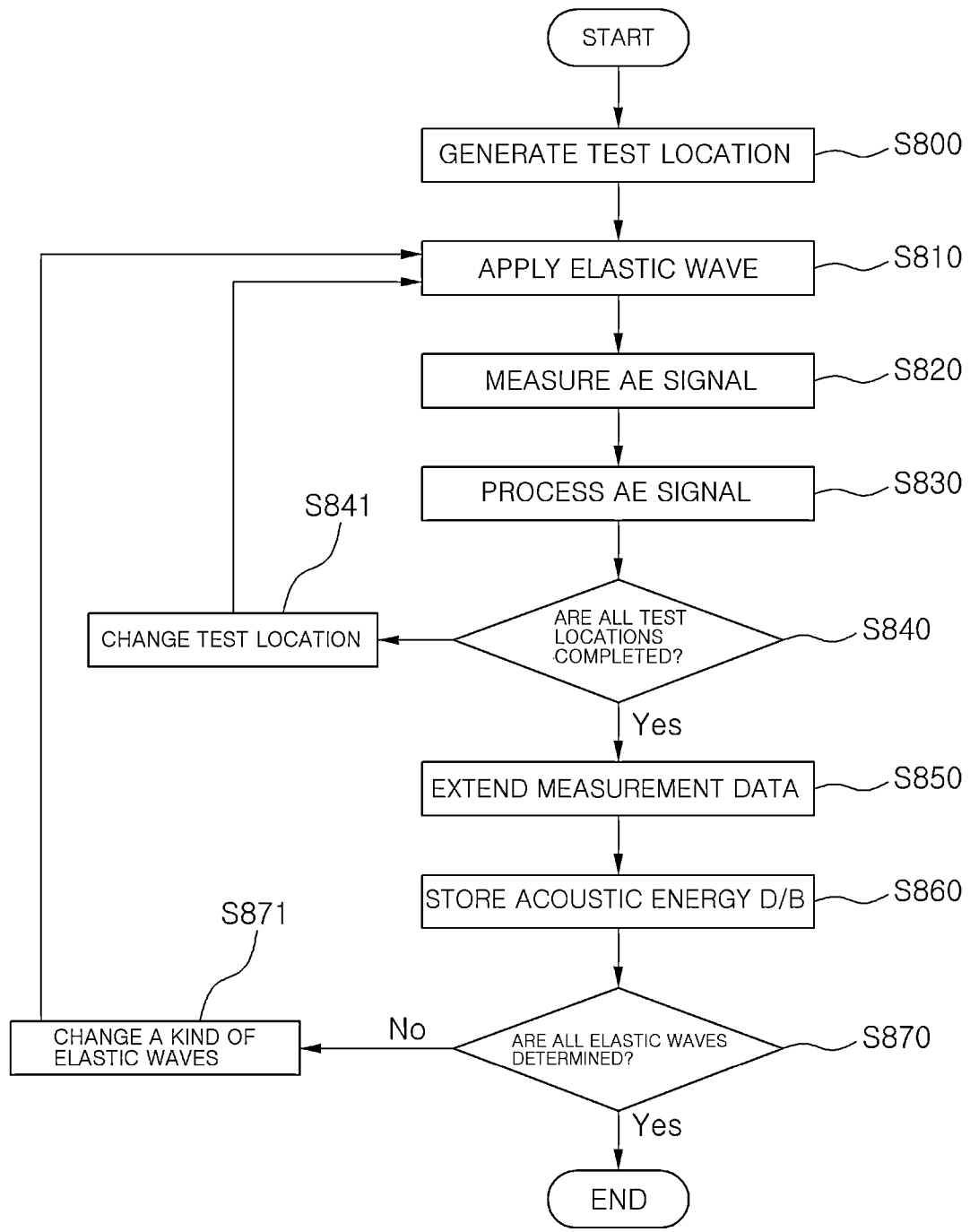
FIG. 8 is a process flow diagram for describing a method for writing contour maps of the method of locating a damage source of the wind turbine blade according to the present invention.
Figure 9:
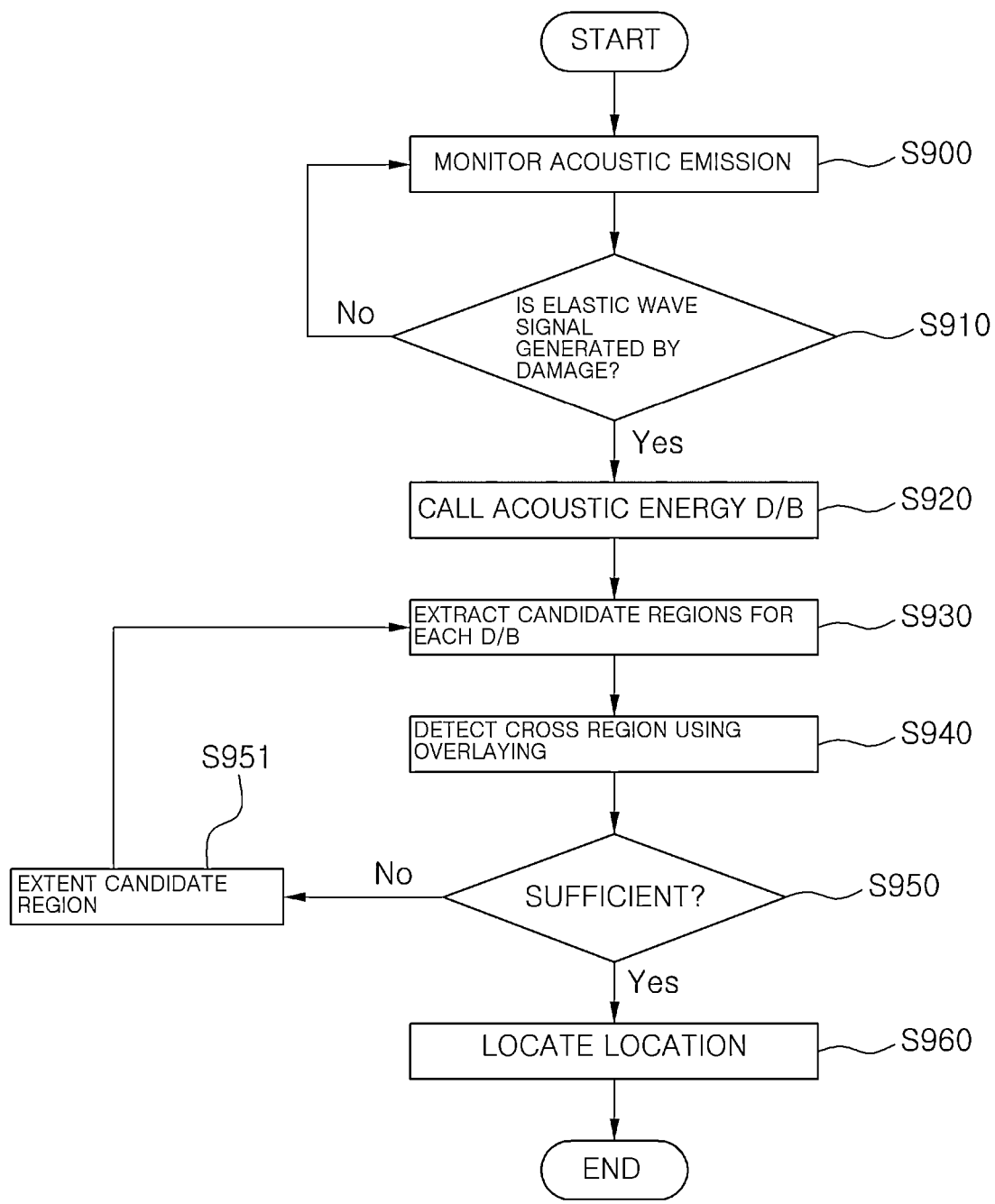
FIG. 9 is a process diagram for describing a method of detecting a damage source location of the method of locating a damage source of the wind turbine blade according to the present invention.

Detailed exemplary embodiments of the present invention will be described with reference to the accompanying drawings. FIG. 3 is a schematic diagram illustrating an apparatus of locating a damage source of a wind turbine blade according to the related art, FIG. 4 is an exemplified diagram of a sample structure and contour maps for configuring a contour map database based on an energy value according to the present invention, and FIG. 5 is an exemplified diagram illustrating contour maps at each AE sensor of the method of locating a damage source according to the present invention. FIG. 6 is an exemplified diagram for describing a mechanism of determining a damage source location of the method of locating a damage source of a wind turbine blade according to the present invention, FIG. 7 is an exemplified diagram for describing a mechanism of expanding a damage source prediction region of the method of locating a damage source of the wind turbine blade according to the present invention, and FIG. 8 is a process flow diagram for describing a method for writing contour maps of the method of locating a damage source of the wind turbine blade according to the present invention. FIG. 9 is a process diagram for describing a method of detecting a damage source location of the method of locating a damage source of the wind turbine blade according to the present invention.

Matters not used to understand technical ideas of the present invention as portions that are not different from the related art are excluded from the description, but the technical ideas and the protective scope of the present invention are not limited thereto.

First, the apparatus of locating a damage source of a wind turbine blade according to the present invention will be described in detail with reference to FIG. 3.

The apparatus of locating a damage source of a wind turbine blade according to the present invention may include: AE sensors 200 that detect acoustic emission signals; an amplification unit 300 that amplifies the detected AE signal to an analyzable size; a signal processor 400 that processes an amplified AE signal; an originating module 500 that wirelessly originates the signal processed AE signal; a receiving module 700 that receives the AE signal from the originating module 500 and transmits the received AE signal to a signal analysis unit 800; and a signal analysis unit 800 that receives the AE signal from the receiving module 700 to locate a damage source.

The AE sensor 200 is a sensor receiving an acoustic emission signal from a stress wave generated when strain energy locally formed in a solid is suddenly emitted, and the like, is suddenly emitted and generally includes a preprocessing amplifier 310 and a main amplifier 320. Preferably, the AE sensor 200 is configured of a piezoelectric sensor.

The AE sensors 200 are installed by basically selecting the most optimized mechanism for measuring a structure and an example thereof is as follows. That is, the AE sensor 200 selects a straight line going across a center of the wind turbine blade 3 so as to be installed at a predetermined distance or as illustrated in FIG. 4(a), the AE sensor 200 is installed by dividing an interest region of the wind turbine blade 3 into any squared shape.

The pre-processing amplifiers 310 are installed for each AE sensor 200 one by one and may be a high pass filter and a low pass filter or a band pass filter configured of a combination thereof.

The main amplifier 320 includes a filter for processing low and high frequency signals and receives and processes the AE signal amplified by the pre-processing amplifiers 310 and output an analog signal in real time.

The signal processor 400 performs appropriate processes such as removing, analyzing, and calculating, and the like, noise of the real-time AE signal transferred from the main amplifier 320 and transfers the processed AE signal to the originating module 500.

The originating module 500 serves to collect the signals from the AE sensors 200 and wirelessly transmit the collected signals to the signal analysis unit 800 located at a long distance. To this end, the originating module 500 is provided with an originating antenna 510. The wind power generator 1 is mainly installed at sea and the wind turbine blade 3 generally rotates by wind power at a high altitude, which cannot be therefore directly connected in a wired line so as to acquire the AE signal. Therefore, the present invention introduces the originating module 500 that transmits a signal wirelessly.

Meanwhile, the apparatus of locating a damage source locating of the wind turbine blade according to the present invention further includes a separate power supply 600 for driving a signal processor 400, the originating module 500, and the amplification unit 300. The AE sensor 200, the amplification unit 300, the signal processor 400, the originating module 500, including the power supply 600, are mounted in the inner space part of the wind turbine blade 3 or installed in the material.

Figure 1:
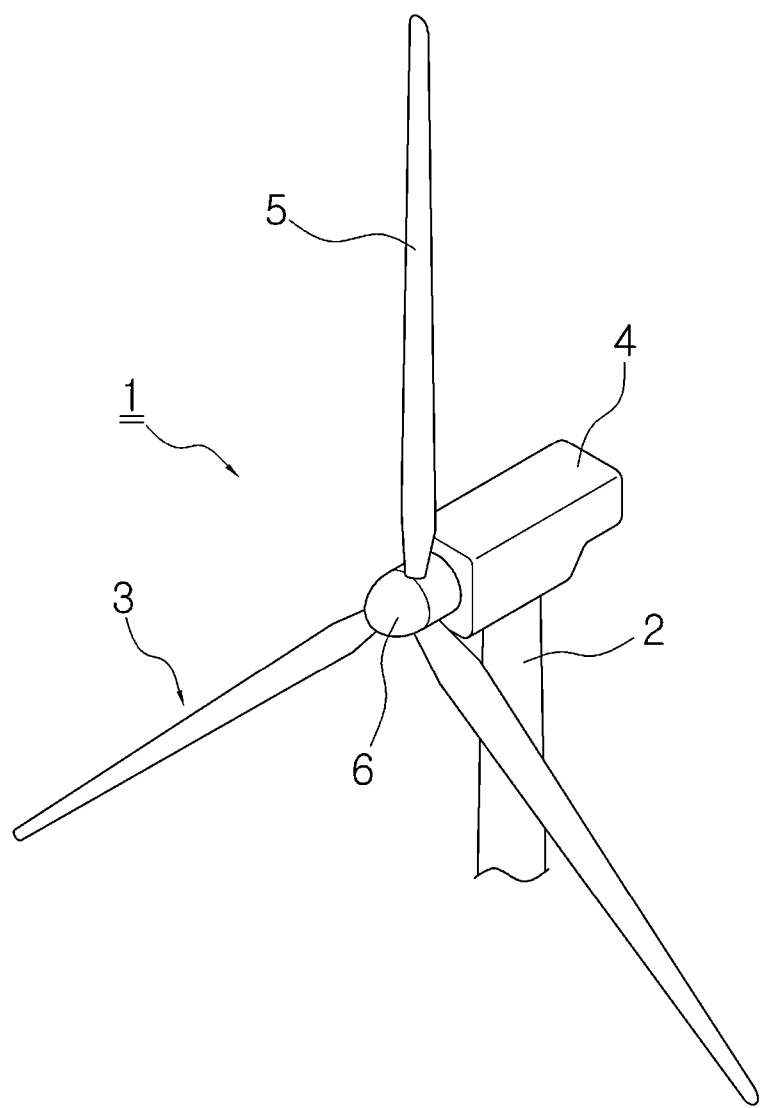
FIG. 1 is a perspective view illustrating a general wind power generator.
Figure 2:
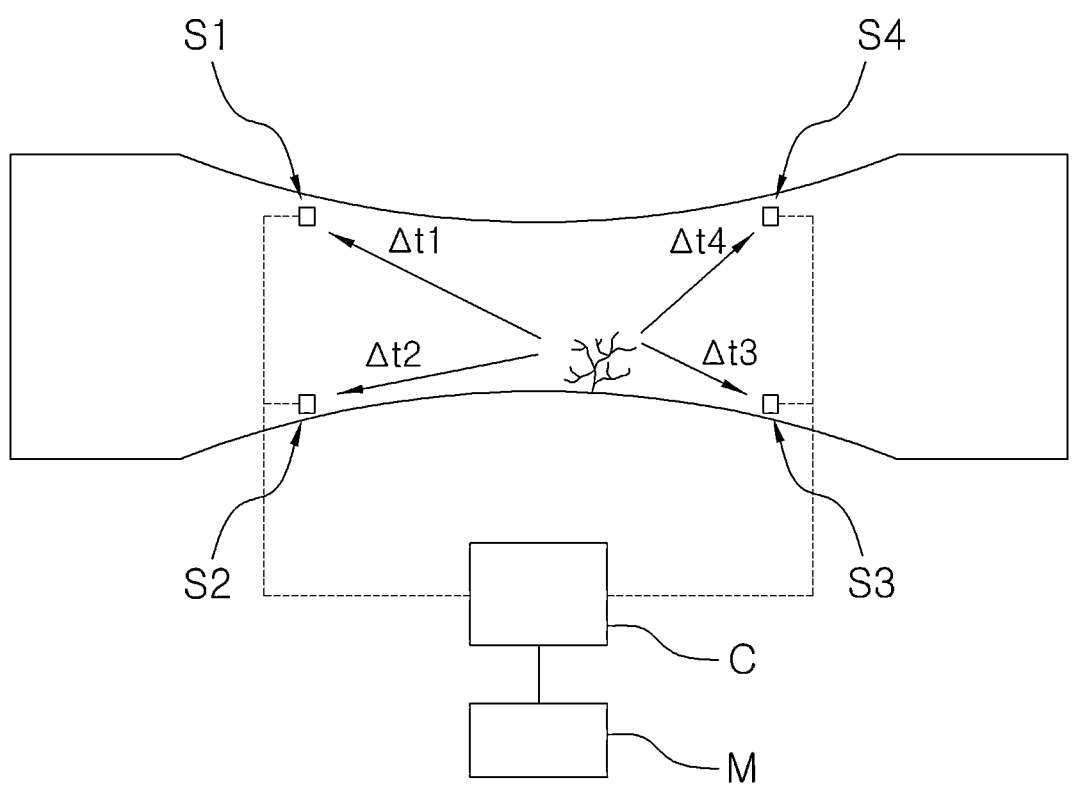
FIG. 2 is a schematic diagram illustrating a method of locating a damage source using acoustic emission according to the related art.

The signal analysis unit 800 is disposed in a remote site that is far away from the wind power generator 1 (FIG. 1). The signal analysis unit 800 includes a receiving module 700 for receiving a digitalized AE signal transmitted by the originating module 500. The receiving module 700 includes a receiving antenna 710. The signal analysis unit 800 uses the measured AE signal to write contour maps based on energy values for each AE sensor 200 and stores the written contour maps in a database and uses the contour maps for each AE sensor 200 to decide the damage source location at the time of sensing an elastic wave generated from actual defects. A mechanism of writing the contour maps and a mechanism of locating a damage source will be described below in detail.

Next, a method for writing contour maps for each AE sensor 200 based on elastic energy among methods of locating a damage source of the wind turbine blade according to the present invention and a method of forming a database using the same will be described with reference to FIGS. 4, 5, and 8.

The writing of the contour maps for each AE sensor 200 means applying an elastic wave for a test to an object under the laboratory, prior to substantially operating the targeted object for locating a damage source and writing a table by writing a transfer aspect of elastic energy in advance based on the AE signal according to the elastic wave. For example, at the time of monitoring the occurrence of damage and searching for the damage source location for a part of the wind turbine blade 3 as an object as illustrated in FIG. 3, the writing of the contour maps for each AE sensor 200 means dividing the portion to be monitored in the laboratory into several points as illustrated in FIG. 4 to apply the elastic wave for a test and writing the contour maps for each AE sensor 200 as illustrated in FIG. 4 (*b*), before the wind turbine blade 3 is installed in the wind power generator 1 and operated.

The contour map database is based on manufacturing an object at the time of the most healthy time and if the object is operated in advance, the time when the database starts to write is assumed as the most healthy state.

For forming the contour map database, the location of the AE sensor 200 suitable for the measurement of the object is first selected and the sensor is installed. Next, as illustrated in FIG. 4A, a square matrix is virtually drawn on an object, that is, a surface of a structure (that is, sample) 900 at a constant interval to define a cross point as test locations 910 and an electric wave having a constant size of energy is generated, which is measured by the AE sensor 200. One AE signal measured by each sensor is integrated by the signal processor 400 or the signal analysis unit 800 to determine the test locations 910 as one representative energy value.

When the measurement of elastic energy according to the application of the elastic wave for each test location 910 on all the matrixes is completed, a matrix including all the whole structure is completed. FIG. 4(*b*) illustrates $N_{0.2}$ (a matrix written by a value transformed into time or frequency based on the AE signal measured by a second sensor and then transformed into an energy value). The energy values for each test location illustrated in FIG. 4(*b*) are an energy value of the AE signal, and therefore are not affected by a threshold value and a change in a mode on an effect of attenuation during the signal propagation process.

The contour map database for each AE sensor 200 stores an energy value of an event of an acoustic emission signal of the measured elastic wave in a matrix form. That is, the elastic wave generated at a specific one test location reaches a sensor through a propagation process and the elastic wave of which the characteristics are changed during the propagation process is signal-processed as the energy value and stored in the matrix as an element. Coordinate (x, y) values for each test location 900 are reduced to element values of (m, n). The matrix $N_o$ having the energy values is completed by repeating this, which is a basic of a database generated in future. The matrix $N_o$ is generated as many as the number of used AE sensors 200.

According to the method of locating a damage source of the wind turbine blade according to the present invention, the (m, n) locations of the database are represented by the results of locating the damage source, such that the matrix $N_o$ is larger expanded than data obtained by measuring the data amount by an interpolation process. The interpolation working is to increase the accuracy of the results of locating the damage source. The matrix $N_o$ creates the N matrix k times as much as the data amount by the interpolation working. The ratio K expanded by the interpolation is determined at an optimal ratio according to a distance between the test locations 910, which may be determined by the comparison at the time of the test of locating the damage source for verifying the database FIG. 4(*c*) illustrate a matrix N2 corresponding to the second AE sensor 200 that is formed by expanding the measurement data based on the interpolation. It can be appreciated that the data distribution may be much softer than that of the original measurement data matrix No FIG. 4B.

The expanded contour maps are prepared for each AE sensor 200 and an example thereof is illustrated in FIG. 5. As can be appreciated from the drawing, the elastic energy distribution is derived as entirely different aspects for each AE sensor 200 and is generated according to a change in a kind of medium as far as a point at which each AE sensor 200 is located, which ironically verifies that the method of locating a damage source using the acoustic emission according to the related art is inaccurate.

Meanwhile, a kind of damages that may occur in the wind turbine blade 3 (FIG. 3) is very various and a spectrum of a size of the elastic energy thereof is also very wide, such that it is difficult for N databases of one group written by a size of one elastic energy to accurately locate the damage source. That is, this makes sense that the torsion damage source location of the wind turbine blade 3 due to a typhoon cannot be detected with the contour map database written by predicting a collision of a tide and applying the elastic wave having a size suitable therefor to the test locations.

To solve the problem, the present invention introduces a method of configuring a plurality of groups of N databases while changing the size of the elastic waves. As illustrated in FIG. 8, N matrix groups are formed by applying a size of one elastic wave to each test location 910 and then another N matrix groups are formed by changing the size of the elastic waves. A determination on applicable groups in the damage source location among a plurality of $N_g$ (herein, g is a group according to the size of the elastic wave) is performed in an algorithm of locating a damage source.

The contour map databases for each size of the elastic wave energy configured as described above, the $N_g$ is stored in the signal analysis unit 800 of FIG. 3 as a text based file format and easily read as data and the contents thereof can be confirmed and accessed even in another program.

Next, the method of locating a damage source of the wind turbine blade according to the present invention will be described in more detail with reference to FIGS. 6, 7, and 9.

The algorithm of locating a damage source is partially very similar to one building the database of the counter map. When a process of building the database is performed in a reverse order, the damage source location can be performed.

As illustrated in FIG. 3, when it is highly likely to cause a damage or when the damage occurs, the AE sensor 200 is installed at a fatal portion to monitor whether there is the acoustic emission due to the damage. The installation location of the AE sensor 200 coincides with the location attached during the process of forming the counter map database and the location of the AE sensor 200. When the elastic wave is generated due to the damage during the monitoring and the energy is measured by the AE sensor 200, the measured AE signal is signal-processed by the same method as the process of building the data base and is transformed into an energy value $E_o$.

Next, the AE sensor 200 suitable for analysis is selected. In case of the wind turbine blade 3, a length of one side of the wind turbine blade 3 is very long, and therefore when a damage occurs at any portion thereof, it is inefficient to analyze the damage using all the sensors disposed at the whole structure. Therefore, it is advantageous to increase accuracy by selecting only the AE sensor 200 sufficiently closed to the damage to be used for location. The AE sensor 200 to be used at the time of the generation of any AE signal compares the elastic energies measured for each sensor to select the largest measured sensors or selects the sensor forming the squared region configured of the sensor having the largest size to perform the damage source location.

When the AE sensor 200 to be used for location is selected, the contour map database N corresponding thereto is extracted. Next, (m, n) coordinates having a value equal to the E, among the elastic energy values stored in the N are extracted to determine damage prediction regions L. The separate contour maps for each AE sensor 200 are included in the database, and therefore the damage prediction regions Ls are determined for each AE sensor 200.

When the process is repeatedly performed on each AE sensor 200, all the damage prediction regions for each sensor are determined. The damage prediction regions overlay each other for each group, and thus the place where the candidate regions of all the AE sensors 200 meet each other due becomes the only a region (x, y) at which the damage occurs.

FIG. 6 illustrates the damage prediction region and the damage occurrence region that are derived during this process. FIGS. 6(a) to 6(d) illustrate that damage occurrence prediction regions 920, 930, 940, and 950 are searched from values stored in N using the elastic energy $E_o$ that is generated by the damage as N for each specific AE sensor (200). Each damage occurrence prediction region 920, 930, 940, and 950 show the (x, y) coordinate values on the actual wind turbine blade 3, and therefore the searched damage occurrence region also means the actual coordinate values.

All the regions other than the test locations 910 are filled with virtual data by the interpolation during the process of building the counter map database, and therefore may not meet the L corresponding to the energy value $E_o$ of the measured damage signal even though all the relays overlay each other. Therefore, in order to secure the high reliability, there is a need to expand the damage prediction region using E values obtained by applying a constant error range to $E_o$. The Ls obtained by using several E values have a wider range, and thus have a high possibility to overlay the damage prediction regions from other AE sensors 200, which is advantageous in searching for the damage source location. The position at which the Ls of all the AE sensors 200 first overlay each other due to the gradually increased error range is determined as the damage occurrence region.

FIG. 7 illustrates an example of the damage prediction region 920 representing the $E_o$ value obtained by applying the error range. It can be appreciated that as the error range is increased, the damage occurrence candidate region 980 is gradually wider.

Meanwhile, the present invention acquires data by variously changing the size of the elastic energy in the test locations 910 (FIG. 4) at the time of building the contour map database, but whether to use the contour map tested by any elastic energy may be determined by the size of the error range as described above.

That is, the error range is gradually increased during the process of determining the damage occurrence region by selecting the databases built for the size of energy of each elastic wave. Among those, it can be considered that the elastic wave energy in which the damage occurrence region is determined as the smallest error range corresponds to the appropriate database. The above algorithm is mounted in the signal analysis unit 800, and thus is appropriately used.

The method of locating a damage source of the wind turbine blade and the apparatus thereof according to the present invention has high accuracy without largely changing the track mechanism and the methodology according to the related art. Therefore, it can be implemented by changing only the software while using the existing measurement equipment as it is.

Next, for describing the advantage of the method of locating a damage source of the wind turbine blade according to the present invention, the real data obtained by applying it to the actual object is proposed.

The structure for test has a shape in which a part of the wind turbine blade 3 is cut and is formed of a composite material by the same manufacturing method as the actual object and the size thereof has a length, a width, and a height of 1500 mm, 1000 mm, and 160 mm. As the AE sensor 200, four R3Is of PAC in 30 kHz belonging to a relatively low frequency band has been used and are disposed at four corners so as to measure the overall region of the sample. In more detail, the locations of each sensor are (0, 100), (0, 700), (1500, 100), and (1500, 700).

As the test locations 910 for applying the elastic wave for test, 144 test locations are selected at an interval of 100 mm in length and breadth. The counter map database is built by changing the size of the elastic wave to three at each location.

The following table shows the relationship between the damage occurrence region derived by the method of locating a damage source of the wind turbine blade according to the present invention and the actual occurring region. In order to emphasize the advantages of the present invention, it was compared with the method of locating a damage source using the acoustic emission according to the related art. The method of locating a damage source according to the related art needs to input the propagation speed but is difficult to specify the propagation speed due to the non-uniform material, and thus measures the propagation speed by three different speeds and shows all the measured results.

TABLE 1

Comparison of error between damage source location according to the present invention and damage source location according to the related art

| Size of elastic energy | Applied location (x, y) | | Locating result according to the related art | | | | | | Locating result according to the present invention (x, y) | | Error according to the related art | Error according to the present invention |
|---|---|---|---|---|---|---|---|---|---|---|---|---|
| | | | v = 1165 m/s | | v = 894 m/s | | v = 753 m/s | | | | | |
| CASE 1 | 1200 | 700 | N/A | N/A | N/A | N/A | 900 | 800 | 1000 | 500 | 316 | 224 |
| CASE 2 | 500 | 0 | N/A | N/A | N/A | N/A | N/A | N/A | 550 | 50 | N/A | 71 |
| CASE 3 | 1100 | 200 | 950 | 150 | 950 | 250 | 800 | 250 | 1350 | 100 | 271 | 269 |

TABLE 1-continued

Comparison of error between damage source location according to the present invention and damage source location according to the related art

| Size of elastic energy | Applied location (x, y) | | Locating result according to the related art | | | | | | Locating result according to the present invention (x, y) | | Error according to the related art | Error according to the present invention |
|---|---|---|---|---|---|---|---|---|---|---|---|---|
| | | | v = 1165 m/s | | v = 894 m/s | | v = 753 m/s | | | | | |
| CASE 4 | 1200 | 500 | 1300 | 450 | 1100 | 450 | 1050 | 450 | 1300 | 550 | 127 | 112 |
| CASE 5 | 900 | 600 | 800 | 550 | N/A | N/A | 650 | 500 | 300 | 300 | 334 | 300 |
| CASE 6 | 1000 | 100 | 850 | 650 | 800 | 550 | 800 | 500 | 1100 | 500 | 196 | 141 |
| CASE 7 | 1100 | 100 | 850 | 200 | 850 | 250 | 825 | 275 | 900 | 100 | 296 | 200 |
| CASE 8 | 700 | 400 | 750 | 375 | 750 | 375 | 750 | 375 | 700 | 400 | 56 | 0 |
| CASE 9 | 300 | 200 | N/A | N/A | 550 | 50 | 600 | 100 | 300 | 100 | 304 | 100 |
| CASE 10 | 1100 | 700 | 900 | 625 | 650 | 625 | 590 | 600 | 1200 | 700 | 249 | 100 |

As the comparison test results, it can be appreciated that the method of locating a damage source according to the present invention shows higher accuracy than the method according to the related art and succeeds to locate the damage sources in all 10 experiments.

Further, one of the important effects of the present invention may include CASE1 and CASE2. It can be appreciated that the method according to the related art fails for all the damages occurring outside the region configured of four AE sensors 200 or shows a considerably large error, while the method of locating a damage source is successful for all of them and shows considerably accurate results. This means that when the present invention is applied to the actual wind turbine blade 3, it can be freely disposed and used without restricting the location and arrangement of the sensor.

FIG. 8 is a process flow diagram for describing a method of writing an elastic energy contour map of the method of locating a damage source of the wind turbine blade according to the present invention. Referring to FIG. 8, the plurality of acoustic emission (AE) sensors 200 are attached on the sample 900 (FIG. 4(a)) so as to surround the portion to be located and the test locations 910 are generated on the structure of the sample 900 (S800). Further, in this case, a process of partitioning the test locations into a lattice type and selecting the test locations 910 at cross points of each lattice is performed. The drawing illustrating this is illustrated in FIG. 4(a).

When the test locations 910 are generated, the elastic waves are applied to each test location (S810).

The elastic wave may be applied by using the AE sensor 200 and by another elastic wave generation means applying the elastic waves.

When the elastic waves are applied, the AE sensor 200 measures the AE signals (S820).

Further, in this process, a process of confirming whether all the AE signals are measured from all the test locations 910 (S830) is performed. In other words, it is confirmed whether the AE signals are properly measured from all the test locations 910.

As the confirmation result, when the AE signals are not measured properly, the elastic waves are applied again by changing the test locations 910 (S831). Further, in this case, S810 to S830 are performed again.

Unlike this, as the confirmation result, when the AE signals are measured properly, the AE signals are processed and the measurement data are extended (S840 and S850).

Herein, the AE signal processing is a process of performing time or frequency transform and obtaining the energy value. For example, an example of the process may include a process of performing a transform into a power spectrum by using fast Fourier transform (FFT).

Further, in this case, the test locations 910 (FIG. 4(a)) are divided into a plurality of intervals, which are determined by the interpolation based on the elastic energy values at the test locations 910.

The transformed elastic energy is databased as the information parameters on each test location 910 and is stored (S860).

Further, a process of determining whether a plurality of elastic waves having different sizes of energy selected as a sample are databased is performed (S870). In other words, the information on each test location 910 is databased as parameters and it is confirmed whether the database for all the elastic waves is performed. In other words, when the elastic waves for each strength 10, $10^1$, $10^2$, $20^3$, $20^4$, and $10^5$ (J) are applied, the database may be built as each five group for each strength of elastic waves.

As the confirmation result, when the database for these elastic waves is not performed, a process of changing a kind of elastic waves and applying the elastic waves is performed again (S871).

Further, it is possible to change and apply the size of the elastic waves.

Unlike this, in S870, when the database for all the elastic waves is completed, the contour map for locating the damage source is built using the acoustic emission.

Further, a process of extending the number of databased elastic energy data and databasing it may be additionally performed.

FIG. 9 is a process flow diagram for describing a method of detecting a damage source location of the method of locating a damage source of the wind turbine blade according to the exemplary embodiment of the present invention. That is, FIG. 9 illustrate a process of performing a method of locating a damage source of the wind turbine blade using data by the database described in FIG. 8.

Referring to FIG. 9, the plurality of AE sensors 200 is attached to the structure applied to the real environment and monitors the acoustic emission (S900).

In the monitoring process, it is confirmed whether the elastic wave signal is generated due to the damage (S910). That is, this process is a process of confirming whether the AE signal is input.

When the AE signals are not input, the acoustic emission monitoring is performed.

Unlike this, when the AE signals are input, the AE signals are transformed into the energy values and the previously generated database is called to extract the test locations 910 corresponding to the elastic wave energy as the damage location prediction regions for each AE sensor 200 (S920 and S930).

When the prediction region is extracted, the cross points are obtained by overlaying the damage location prediction regions and the cross points are determined as the damage occurrence locations (S940).

In this case, it is confirmed that the determined damage occurrence locations are certainly sufficient (S950). That is, in the S940, it is confirmed whether the cross points are obtained.

A the confirmation result, when the determined damage occurrence is not sufficient, the error range is given to the transformed elastic energy value to transform the given elastic energy value into a new elastic energy value and then extend the damage prediction region and call the generated database again to extract the prediction region (S951). In this case, S930 to S950 are performed again.

Unlike this, as the confirmation result in S950, when the determined damage occurrence locations are certain, the damage source location is determined (S960).

The exemplary embodiment of the present invention as described above described the wind turbine blade of the generator to help understand the present invention but is not limited thereto. For example, the embodiment of the present invention can be applied to another type of large composite material structure. As an example, there may be an airplane structure, a building structure, and yacht structure, and the like.

The present invention is not limited to the aforementioned exemplary embodiment and an application range is various and it is apparent that various modifications can be made to those skilled in the art without departing from the spirit of the present invention described in the appended claims.

The invention claimed is:

1. A method of building a contour map for a damage source location in a nondestructive way using acoustic emission, comprising:
   a first step of attaching at least two acoustic emission (AE) sensors within a portion to be located;
   a second step of generating test locations in a structure to be located;
   a third step of applying elastic waves to each of the test locations;
   a fourth step of measuring acoustic emission (AE) signals by each of the AE sensors;
   a fifth step of transforming the measured AE signals into times or frequencies and then into energy values; and
   a sixth step of databasing the transformed energy values as parameters of information on the each of the test locations,
   wherein the second step comprises: a step of partitioning the structure into lattices using the AE sensors and a step of selecting cross points of the lattices as the test locations,
   the third step comprises: a step of applying the elastic waves to each of the test locations two or more times by changing a size of each of the elastic waves, and
   the sixth step comprises: a step of databasing the transformed energy values as the parameters according to the size of each of the elastic waves.

2. The method of claim 1, wherein in the sixth step, the transformed energy values based on coordinates of the cross points are databased.

3. The method of claim 1, further comprising:
   a seventh step of extending the number of energy value data databased in the sixth step,
   wherein in the seventh step, data extension is made by dividing the test locations at a plurality of intervals and interpolation is performed based on an energy value at the test locations.

4. A method of locating a damage source in a nondestructive way using acoustic emission, comprising:
   a first step of applying elastic waves to test locations of a structure to be located two or more times by changing sizes of the elastic waves to database measured energy values as the test locations for each acoustic emission (AE) sensor according to each size of the elastic waves;
   a second step of attaching the plurality of AE sensors to a structure applied to an actual environment to monitor acoustic emission;
   a third step of transforming a signal into an energy value when the AE signal is input;
   a fourth step of calling the data base of the first step to extract damage location prediction regions for each AE sensor corresponding to the energy values;
   a fifth step of overlaying damage source prediction regions for each AE sensor to obtain cross points and determining the cross points as damage occurrence locations, and
   a sixth step of extending the damage prediction regions returning to the fourth step again after an error range is given to the elastic energy values of the third step to transform the given elastic energy values into new elastic energy values when the cross points are not obtained in the fifth step.

5. The method of claim 4, wherein the elastic waves of the first step are applied in different sizes so as to be databased and the damage prediction region extension of the sixth step is formed for each database for the size of the elastic waves, such that the final damage occurrence locations are determined from the database having a minimum error range.

6. A method of locating a damage source in a nondestructive way using acoustic emission, comprising:
   a first step of attaching at least two acoustic emission (AE) sensors within a portion to be located;
   a second step of generating test locations in a structure to be located;
   a third step of applying elastic waves to each test location;
   a fourth step of measuring acoustic emission (AE) signals with each AE sensor;
   a fifth step of transforming the measured AE signals into time or frequency and then transforming the transformed AE signals into energy values;
   a sixth step of databasing the transformed energy values as parameters of information on each test locations;
   a seventh step of attaching the plurality of AE sensors to a structure applied to the actual environment to monitor acoustic emission;
   when the AE signals are input, an eighth step of transforming the signals into the energy values;
   a ninth step of calling a database of the sixth step to extract the called database as damage source prediction regions for each AE sensor corresponding to the elastic energy of the eighth step; and
   a tenth step of overlaying the damage source prediction region to obtain cross points and determine the cross points as the damage source occurrence locations, wherein the second step comprises: a step of partitioning each test location into lattices using the AE sensor and a step of selecting cross points of each lattice as the test locations, in the third step, the elastic waves are applied to each test location two or more times by changing each size of the elastic waves, and in the sixth step, the energy values for each test location are databased as the parameters according to each size of the elastic waves, and when the cross points are not obtained in the tenth step, an error range is given to the energy values of the eight step to transform the given energy values into new elastic energy values, and then the step returns to the ninth step again.

* * * * *